(12) United States Patent
Managoli

(10) Patent No.: US 7,344,738 B2
(45) Date of Patent: Mar. 18, 2008

(54) HERBAL COMPOSITION FOR TREATMENT OF IMMUNOCOMPROMISED CONDITIONS

(75) Inventor: Nandkishor Bapurao Managoli, Gujarat (IN)

(73) Assignee: Sahajanand Biotech Pvt. Ltd., Gujarat (IN)

( * ) Notice: Subject to any disclaimer, the term of this patent is extended or adjusted under 35 U.S.C. 154(b) by 146 days.

(21) Appl. No.: 11/287,853

(22) Filed: Nov. 28, 2005

(65) Prior Publication Data

US 2007/0122496 A1  May 31, 2007

(51) Int. Cl.
*A01N 65/00* (2006.01)
*A61K 9/48* (2006.01)
*A61K 9/20* (2006.01)

(52) U.S. Cl. .............. 424/725; 424/195.17; 424/754; 424/757; 424/758; 424/769; 424/451; 424/464; 514/885

(58) Field of Classification Search .............. None
See application file for complete search history.

(56) References Cited

U.S. PATENT DOCUMENTS 5,595,796 A * 1/1997 Hammer et al.

OTHER PUBLICATIONS

Narod, SA. Oncogene (2006), 25(43): 5832-5836. Modifiers of risk of hereditary breast cancer.*

Yarden, RI et al. Molecular Cancer Therapeutics (2006)m 5(6):1396-1401. BRCA1 at the crossroad of multiple cellular pathways: approaches for therapeutic interventions.*

Dietert, RR et al. Current Medicinal Chemistry (2006), 16(3): 1075-1085. Early-life immune insult and developmental immunotoxicity (DIT)-associated diseases: potential of herbal- and fungal-derived medicinals.*

* cited by examiner

*Primary Examiner*—Michele Flood
(74) *Attorney, Agent, or Firm*—Volpe & Koenig PC

(57) ABSTRACT

A pharmaceutical or medicinal preparation comprising a combination of two herbal compositions to be administered together. The first herbal composition comprises a mixture of the following herbs: *Asparagus racemosa, Curcuma longa, Glycyrrhiza glabra, Momordica charantia, Tinospora cordifolia, Withania somnifera, Spirulina, Allium sativum, Emblica officinalis, Terminalia belerica,* and *Terminalia chebula*, or a mixture of the active ingredients that have been extracted from those herbs or chemically synthesized. The second herbal composition comprises a mixture of the following herbs: *Moringa oleifera, Boerhavia diffusa, Onosma bracteatum, Bauhinia variegata, Spheranthus indicus, Tecomella undulata, Chlorophytum borivilianum, Ficus racemosa,* and *Cyperus rotundus*, or a mixture of the active ingredients that have been extracted from those herbs or chemically synthesized. The herbal preparation is effective for the treatment a wide range of physiological and pathological conditions in the human body resulting from a weakened or deteriorating immune system.

19 Claims, No Drawings

HERBAL COMPOSITION FOR TREATMENT OF IMMUNOCOMPROMISED CONDITIONS

FIELD OF INVENTION

This invention relates to a herbal formulation which has been found to be effective in improving the immune response in individuals exhibiting immunocompromised conditions. The present invention particularly relates to an herbal preparation comprising a blend of extracts of medicinal herbs and their active ingredients which are effective for improving the immune response in individuals having conditions in which the immune system is debilitated, and stimulating and modulating the immune system to control other conditions that may result due to a weakened immune system.

BACKGROUND

Individuals affected with conditions such as cancer, human immunodeficiency virus (HIV), acquired immune deficiency syndrome (AIDS), old age, or other physiological and pathological conditions, typically exhibit a weakened immune response. Consequently, individuals having a weakened immune system are prone to acquiring other harmful diseases or conditions. Individuals affected with conditions such as cancer, HIV, AIDS, old age, etc., are conventionally treated with drugs or by therapy, including radiation or chemotherapy, which often have adverse side effects, and add to the individual's weakened immune condition.

There is a need for improved medicinal preparations for use in the treatment or regulation of such physiological and pathological conditions, without the adverse toxic effects associated with conventional modes of treatment of such conditions. It is an object of the present invention to provide such a preparation.

SUMMARY

The present invention is directed to a pharmaceutical or medicinal preparation comprising a combination of two herbal compositions to be administered together. The first herbal composition comprises a mixture of the following herbs: *Asparagus racemosa, Curcuma longa, Glycyrrhiza glabra, Momordica charantia, Tinospora cordifolia, Withania somnifera, Spirulina, Allium sativum, Emblica officinalis, Terminalia belerica,* and *Terminalia chebula*, or a mixture of the active ingredients that have been extracted from those herbs or chemically synthesized. The second herbal composition comprises a mixture of the following herbs: *Moringa oleifera, Boerhavia diffusa, Onosma bracteatum, Bauhinia variegata, Spheranthus indicus, Tecomella undulata, Chlorophytum borivilianum, Ficus racemosa,* and *Cyperus rotundus*, or a mixture of the active ingredients that have been extracted from those herbs or chemically synthesized. The herbal preparation is effective for the treatment a wide range of physiological and pathological conditions in the human body resulting from a weakened or deteriorating immune system.

One aspect of the present invention is directed to a pharmaceutical or medicinal preparation comprising a first mixture of herbs comprising: *Asparagus racemosa* in an amount of about 12.0-14.6% by weight, *Curcuma longa* in an amount of about 12.0-14.6% by weight, *Glycyrrhiza glabra* in an amount of about 12.0-14.6% by weight, *Momordica charantia* in an amount of about 12.0-14.6% by weight, *Tinospora cordifolia* in an amount of about 12.0-14.6% by weight, *Withania somnifera* in an amount of about 12.0-14.6% by weight, *Spirulina* in an amount of about 6.1-7.5% by weight, *Allium sativum* in an amount of about 6.0-7.4% by weight, *Emblica officinalis* in an amount of about 2.4-3.0% by weight, *Terminalia belerica* in an amount of about 1.8-2.2% by weight, and *Terminalia chebula* in an amount of about 1.8-2.2% by weight; and a second mixture of herbs comprising: *Moringa oleifera* in an amount of about 13.9-16.9% by weight, *Boerhavia diffusa* in an amount of about 14.1-16.1% by weight, *Onosma bracteatum* in an amount of about 12.6-15.8% by weight, *Bauhinia variegata* in an amount of about 10.8-13.2% by weight, *Spheranthus indicus* in an amount of about 9.0-11.0% by weight, *Tecomella undulate* in an amount of about 9.0-11.0% by weight, *Chlorophytum borivilianum* in an amount of about 9.0-11.0% by weight, *Ficus racemosa* in an amount of about 9.0-11.0% by weight, and *Cyperus rotundus* in an amount of about 3.6-4.4% by weight.

DETAILED DESCRIPTION OF THE PREFERRED EMBODIMENTS

According to the present invention there is provided pharmaceutical or medicinal preparation comprising a combination of two herbal compositions to be administered together. The first herbal composition comprises a mixture of the following herbs: *Asparagus racemosa, Curcuma longa, Glycyrrhiza glabra, Momordica charantia, Tinospora cordifolia, Withania somnifera, Spirulina, Allium sativum, Emblica officinalis, Terminalia belerica,* and *Terminalia chebula*, or a mixture of the active ingredients that have been extracted from those herbs or chemically synthesized. The second herbal composition comprises a mixture of the following herbs: *Moringa oleifera, Boerhavia diffusa, Onosma bracteatum, Bauhinia variegata, Spheranthus indicus, Tecomella undulata, Chlorophytum borivilianum, Ficus racemosa,* and *Cyperus rotundus*, or a mixture of the active ingredients that have been extracted from those herbs or chemically synthesized. As well recognized in the art, the term "Spirulina" is the common name used to refer to cyanobacteria selected from the species Arthrospora platensis and Arthrospora maxima. Thus, the term "Spirulina" as used herein refers to either species Arthrospora platensis or Arthrospora maxima or a mixture of both species.

It is an important aspect of the combination herbal preparation of the present invention that it contains a mixture of herbs, or extracts of herbs, rather than a single herb. An unexpected synergistic effect is exhibited by the various ingredients of the herbal preparation of the present invention. The strategic combination of herbs of the present invention exhibits beneficial pharmacological activities when optimally combined as discussed herein. The active ingredients of the herbs are preferably combined in such a manner to optimize and enhance the pharmacological effects with minimal or no adverse toxic reactions (which become a distinct possibility if the herbs are used singly in a concentration of 100%). The advantage of the polyherbal formulation also minimizes the risk of development of drug resistance. The herbal preparations will be discussed herein as exhibiting a synergistic effect when the two compositions are administered together. However, it should be appreciated that the ingredients of the two herbal compositions could be combined into a single herbal composition to exhibit the same synergistic effect.

The ingredients and preferred proportions of herbs in each herbal composition according to the present invention are set forth in Tables 1 and 2. It should be appreciated that that the proportions of the individual herbs may be varied. In particular, the proportions of one or more of the components may be varied in order to optimize the pharmacological effects produced by the formulation to suit the specific needs of the patient being treated.

TABLE 1

Formulation of herbal composition 1

| Botanical Name | Common Name | Part Used | Bio-Markers | Percent By Weight |
|---|---|---|---|---|
| Asparagus racemosa | Shatavari | Root | Saponins > 15% | 12.0-14.6%, preferably 13.3% |
| Curcuma longa | Turmeric | Rhizome | Vol Oil > 10% Curcumin > 10% | 12.0-14.6%, preferably 13.3% |
| Glycyrrhiza glabra | Licorice (Jati madh) | Root | Glycyrrhizen by garratt method > 15-24% | 12.0-14.6%, preferably 13.3% |
| Momordica charantia | Bitter melon (Karela) | Fruit | Bitters > 2.5% | 12.0-14.6%, preferably 13.3% |
| Tinospora cordifolia | Indian tinospora (Guduchi) | Root | Bitters > 1.5% | 12.0-14.6%, preferably 13.3% |
| Withania somnifera | Ashwagandha | Root | Withanolides > 2.5% | 12.0-14.6%, preferably 13.3% |
| Spirulina | Spiropetalum Heterophyllum (Spirulina) | Whole plant | 62% amino acid(V-B-12) | 6.1-7.5%, preferably 6.8% |
| Allium sativum | Garlic | Bulb | Allin 1.5-2.5% by HPLC | 6.0-7.4%, preferably 6.7% |
| Emblica officinalis | Amla | Fruit | Tannis > 20% Ellagic acid > 5% | 2.4-3.0%, preferably 2.7% |
| Terminalia bellerica | Belleric myrobalan (Bahera) | Leaf | Tannins > 10% | 1.8-2.2%, preferably 2.0% |
| Terminalia chebula | Chebulic myrobalan (Harir) | Fruit | Tannins 20-40% | 1.8-2.2%, preferably 2.0% |

TABLE 2

Formulation of herbal composition 2

| Botanical Name | Common Name | Part Used | Bio-Markers | Percent By Weight |
|---|---|---|---|---|
| Moringa oleifera | Horseradish tree (Soanjan) | Bark | Glycosides > 5% | 13.9-16.9%, preferably 15.4% |
| Boerhavia diffusa | Boerhavia (Punarnava) | Root | Alkaloids 0.01-0.08% | 14.1-16.1%, preferably 14.6% |
| Onosma bracteatum | Yunnan onosma (Ratanjot) | Root | Alkaline 1% | 12.6-15.8%, preferably 14.0% |
| Bauhinia variegata | Orchid tree (Kachnar) | Bark | Tannins 25% | 10.8-13.2%, preferably 12.0% |
| Sphaeranthus indicus | Indian sphaeranthus (Gorakhmundi) | Root | Alkaloids 0.5% | 9.0-11.0%, preferably 10.0% |
| Tecomella undulata | Rohida tree (Rohu) | Bark | Tannins 10% | 9.0-11.0%, preferably 10.0% |
| Chlorphytum borivilianum | Chlorophytum (Safed musali) | Root | Saponins > 15% | 9.0-11.0%, preferably 10.0% |
| Ficus racemosa | Cluster fig (Gular) | Leaf | Tannins 10% | 9.0-11.0%, preferably 10.0% |
| Cyperus rotundus | Cyperus (Nagarmoth) | Root | Alkaloids 0.15-0.5% | 3.6-4.4%, preferably 4.0% |

The combination herbal preparation of the present invention can be used as an alternative to conventional drugs or treatments and has been found to effectively treat or maintain a wide range of physiological and pathological conditions in the human body. For example, the combination herbal preparation of the present invention has been found to be particularly useful in maintaining the normal physiological functions of the immune system, in regulating the immunological functions and all the aberrations that occur due to the subtle immunological imbalances and reduced immunity, and to restore and improve the immune function in individuals exhibiting a weakened or deteriorating immune response.

The combination herbal preparation of the present invention has been found to have beneficial effects and to improve the quality of life in individuals experiencing all types of cancer, especially those that directly weaken the immune system, in individuals affected with HIV and AIDS, in individuals exhibiting failing immunity due to old age, and all other conditions of the human body that negatively affect the immune system.

The combination herbal preparation of the present invention exhibits beneficial effects in individuals having cancer, HIV or AIDs, and other immune deficiency conditions at the molecular and enzymatic levels through the following mechanisms: (1) by stimulating the production of growth factors responsible for production of the cells of the immune apparatus, like lymphocytes, macrophages, Langerhans cells, histiocytes, etc.; (2) by enhancing the immune response due to the production of new cells and replacing the aging and functionally incompetent cells of the immune system; (3) by mopping up the free radicals generated by the metabolism of cancer cells, the anti-retroviral metabolism in cells of individuals affected with HIV or AIDS, and during the aging process (i.e. antioxidant effect); and (4) by stimulating the immune apparatus to produce antibodies and to form immune complexes (i.e. immunostimulatory effect).

The combination herbal formulation of the present invention also serves as a preventative treatment to prevent cancer or tumors from forming in genetically or environmentally susceptible individuals. The combination herbal preparation can also be used as a chemoprotective or radioprotective agent in individuals affected with cancer, wherein it can be used as an adjuvant to conventional treatments, such as chemotherapy and radiotherapy, to reduce the adverse side effects of these therapies.

The combination herbal preparation of the present invention also exhibits radiosensitizing and chemosensitizing adaptogenic effects in cancer patients by enabling the tumor to become more sensitive to the effects of these two standard modalities of conventional anticancer therapy. Improved sensitivity of the tumor to radiotherapy and chemotherapy also helps in effectively reducing the required dosage of these therapies in order to achieve the prescribed therapeutic effects, thereby reducing and alleviating the powerful and devastating adverse toxic effects exerted by radiotherapy and chemotherapy in cancer treatment.

The herbal preparations of the present invention have also exhibited efficacy in individuals having cancer, HIV or AIDs, and other immune deficiency conditions as a method of palliative care, as an antistress and anxiolytic, and as an adaptogen, in order to improve the quality and longevity in individuals affected with such conditions.

The herbal preparations of the present invention have also exhibited beneficial effects in stimulating and maintaining the immune system in ill individuals, especially those affected with cancer, HIV or AIDs, and other immune deficiency conditions, or conditions that develop as a result of a weakened immune system, such as chronic fatigue syndrome and allergic conditions. An overall improvement of the quality of life in individuals treated with such preparations has been exhibited by improving the subjective sense of well-being, improving appetite, increasing body weight, alleviating anxiety, improving the ambulatory capacity, mopping up the toxic free radicals generated by cancer metabolism or HIV metabolism (i.e. antioxidant effect). The sum of these effects restore health, vigor and enthusiasm in patients and increase the longevity of patients suffering from cancer, HIV or AIDS, or other immune deficiency conditions, especially in the terminal stages, where conventional therapeutic modalities have been exhausted and there is a rapid fall in the quality of life, necessitating a gentler and more persuasive method to revive the metabolism and serve as an effective method for palliative care.

The combination treatment of the two herbal compositions of the present invention is also useful in rejuvenating, revitalizing, and replenishing the immune system in elderly individuals when there is a physiological reduction in the immune response.

The combination herbal preparation of the present invention, through its immunostimulant and immunomodulator properties, can also alleviate allergic conditions, in particular pollen allergy, uticaria, skin rash, and all such similar conditions.

The manufacture of the herbal compositions and treatment with the combination herbal preparation according to the present invention will now be illustrated by the following example. However, it will be appreciated by one of ordinary skill in the art that the proportions of ingredients, amount of ingredients, and form of administration can vary without departing from the spirit of this invention.

EXAMPLES

Method of Extraction and Manufacture

A polyherbal formulation was prepared in accordance with the present invention by harvesting and cleaning each of the raw herbal ingredients, grinding each ingredient to a fine powder form, diluting each ingredient, and subjecting each of the herbal ingredients to standard solvent extraction methods, including alcoholic and hydroalcoholic solvent extraction, FREON™ gas extraction, $CO_2$ gas extraction, or any other suitable extraction method.

By way of illustration only, the extraction can be performed by using volatile Freon gas. This process has the advantage of being fast and also has the ability to preserve the active chemicals (alkaloids, non-alkaloids, electrolytes, minerals, etc.) in their natural form (as it does not involve heating and denaturation at any stage of the process). Freon, being a highly volatile compound with its boiling point at −21° C., evaporates totally after extraction yielding an ultrapure concentrate of the herbal ingredients.

After extraction, the concentrated extracts were recovered, filtered, and dried. The herbal ingredients were then mixed into the following two compositions:

| Herbal Composition 1 | | |
| --- | --- | --- |
| Botanical Name | Percent By Weight | Mg/Capsule |
| Asparagus racemosa | 13.3% | 99.75 mg |
| Curcuma longa | 13.3% | 99.75 mg |
| Glycyrrhiza glabra | 13.3% | 99.75 mg |
| Momordica charantia | 13.3% | 99.75 mg |
| Tinospora cordifolia | 13.3% | 99.75 mg |
| Withania somnifera | 13.3% | 99.75 mg |
| Spirulina | 6.8% | 51.0 mg |
| Allium sativum | 6.7% | 50.25 mg |
| Emblica officinalis | 2.7% | 20.25 mg |
| Terminalia bellerica | 2.0% | 15.0 mg |
| Terminalia chebula | 2.0% | 15.0 mg |

| Herbal Composition 2 | | |
| --- | --- | --- |
| Botanical Name | Percent By Weight | Mg/Capsule |
| Moringa oleifera | 15.4% | 115.5 mg |
| Boerhavia diffusa | 14.6% | 109.5 mg |
| Onosma bracteatum | 14.0% | 105.0 mg |
| Bauhinia variegata | 12.0% | 90.0 mg |
| Sphaeranthus indicus | 10.0% | 75.0 mg |
| Tecomella undulata | 10.0% | 75.0 mg |

-continued

Herbal Composition 2

| Botanical Name | Percent By Weight | Mg/Capsule |
| --- | --- | --- |
| *Chlorphytum borivilianum* | 10.0% | 75.0 mg |
| *Ficus racemosa* | 10.0% | 75.0 mg |
| *Cyperus rotundus* | 4.0% | 30.0 mg |

After mixing, each herbal composition was individually blended in an automatic blender in order to prepare a homogenous mixture of the herbal ingredients. Each individually blended and homogenized mixture was filled in gelatin capsules in quantities of 750 mg.

It will be appreciated by one of ordinary skill in the art that the amount of the herbal compositions per capsule may vary depending on the individual, the condition being treated, or the frequency of dosage. It will be further understood by one of ordinary skill in the art that the herbal compositions according to the present invention can be prepared together as a single composition, and administered in accordance with any conventional form of administration, including, without limitation, a liquid or syrup, capsule, or tablet.

Toxicity Tests

Acute oral toxicity was conducted using Sprague Dawley rats by administering them the herbal medicine. A single loading dose of 2000 mg/kg body weight was given to the rats to assess its effects on the rats. No signs of toxicity were observed, and there were no instances of mortality in any of the rats treated with the formulation.

Case 1: A Case Report of Cancer

The patient was a fifty-two (52) year old female previously diagnosed with cancer of the left ovary, and had reported recurrence at the primary site of the tumor and the appearance of new metastatic deposits in multiple distant organs, such as the liver and lungs. The patient had completed all the prescribed conventional modalities of cancer therapy, including, surgery, radiotherapy, chemotherapy and hormone therapy.

After completing standard tests such as a complete hemogram, hepatic and renal profiles, and radiological studies to map the extent of disease, the patient was treated with the herbal formulation of the present invention beginning in March 2004. The patient was examined and followed up on a monthly basis to monitor the progress.

The patient had experienced chronic fatigue, malaise, loss of appetite, anorexia, loss of weight and anxiety before initiation of the herbal therapy. The patient experienced significant changes and improvement in quality of life after completion of one (1) month of treatment with the combination herbal preparation of the present invention. The patient exhibited improvements in her appetite, vigor, and enthusiasm, gained 1.0 kg weight, and also reported alleviation of her anxiety. The patient's level of hemoglobin exhibited an increase of 1.2 gm %.

The patient's latest report was prepared in June 2005 and showed a marked improvement in her overall quality of life. The patient gained a total of 4.1 kgs over the prior six (6) month period during treatment with the present herbal composition. The patient's appetite has continued to increase, and there is no complaint of fatigue, malaise, or anxiety. The patient's level of hemoglobin improved by 3.0 gm %, and has been stable at a level of 13.3 gm % over the prior (3) month period. The patient's tumor size has regressed marginally by 0.9 cm since initiating treatment.

These therapeutic effects can be directly attributed to the anticancer, antitumor, immunomodulator, anxiolytic and adaptogenic effects of the combination herbal preparation of the present invention.

Case 2: A Case Report of HIV-AIDS:

The patient was a twenty-eight (28) year old female previously diagnosed with HIV-AIDS in approximately August 2003. The patient was a mother of four (4) young children and had previously lost her husband to the same disease. Prior to initiating treatment, the patient had reported reoccurrence of symptoms of failing immunity, such as loss of appetite, fatigue, loss of weight, reduced performance status (i.e. Karnofsky performance status), prolonged fever, diarrhea, malaise, reduced CD4 counts to only eighty (80) cells, and a high viral load.

After completing standard tests such as a complete hemogram, hepatic and renal profiles, and radiological studies to map the extent of disease, the patient was treated with the herbal formulation of the present invention beginning in August 2004. The patient was examined and followed up on a monthly basis to monitor the progress.

The patient experienced significant changes and improvement in quality of life after completion of one (1) month of treatment with the combination herbal preparation of the present invention. The patient exhibited improvements in her appetite, vigor, and enthusiasm, gained 1.4 kg weight, and also reported alleviation of her anxiety. The patient's level of hemoglobin exhibited an increase of 1.9 gm %.

The patient's latest report was prepared in June 2005 and showed a marked improvement in her overall quality of life. The patient gained a total of 5.4 kgs over the prior six (6) month period during treatment with the present herbal composition. The patient's appetite has continued to increase, and there is no complaint of fatigue, malaise, or anxiety. The patient's level of hemoglobin improved by 3.2 gm %, and has been stable at a level of 13.0 gm % over the prior (3) month period. As a result of the treatment, the patient's CD4 counts were raised to normal levels (i.e. above 500 cells), and the patient's HIV viral load decreased, indicating an improvement of the patient's immune response.

These therapeutic effects can be directly attributed to the immunostimulant, anxiolytic, antioxidant, and adaptogenic effects of the combination herbal preparation of the present invention.

It will be appreciated to those of ordinary skill in the art that changes could be made to the embodiments described above without departing from the broad inventive concept thereof. It is understood, therefore, that this invention is not limited to the particular embodiments disclosed, but is intended to cover modifications within the spirit and scope of the present invention as defined by the appended claims.

What is claimed is:

1. A pharmaceutical or medicinal herbal composition comprising a mixture of herbs comprising: *Asparagus racemosa, Curcuma longa, Glycyrrhiza glabra, Momordica charantia, Tinospora cordifolia, Withania somnifera, Spirulina, Allium sativum, Emblica officinalis, Terminalia belerica,* and *Terminalia chebula.*

2. The pharmaceutical or medicinal herbal composition of claim 1, wherein the composition comprises:

*Asparagus racemosa* in an amount of about 12.0-14.6% by weight of the total weight of the composition;

*Curcuma longa* in an amount of about 12.0-14.6% by weight of the total weight of the composition;

*Glycyrrhiza glabra* in an amount of about 12.0-14.6% by weight of the total weight of the composition;

*Momordica charantia* in an amount of about 12.0-14.6% by weight of the total weight of the composition;

*Tinospora cordifolia* in an amount of about 12.0-14.6% by weight of the total weight of the composition;

*Withania somnifera* in an amount of about 12.0-14.6% by weight of the total weight of the composition;

*Spirulina* in an amount of about 6.1-7.5% by weight of the total weight of the composition;

*Allium sativum* in an amount of about 6.0-7.4% by weight of the total weight of the composition;

*Emblica officinalis* in an amount of about 2.4-3.0% by weight of the total weight of the composition;

*Terminalia belerica* in an amount of about 1.8-2.2% by weight of the total weight of the composition; and

*Terminalia chebula* in an amount of about 1.8-2.2% by weight of the total weight of the composition.

3. The pharmaceutical or medicinal herbal composition of claim 1, wherein the mixture of herbs comprises a mixture of active ingredients that have been extracted from the herbs.

4. A pharmaceutical or medicinal herbal composition comprising a mixture of herbs comprising: *Moringa oleifera, Boerhavia diffusa, Onosma bracteatum, Bauhinia variegata, Sphaeranthus indicus, Tecomella undulata, Chlorophytum borivilianum, Ficus racemosa,* and *Cyperus rotundus.*

5. The pharmaceutical or medicinal herbal composition of claim 4, wherein the composition comprises:

*Moringa oleifera* in an amount of about 13.9-16.9% by weight of the total weight of the composition;

*Boerhavia diffusa* in an amount of about 14.1-16.1% by weight of the total weight of the composition;

*Onosma bracteatum* in an amount of about 12.6-15.8% by weight of the total weight of the composition;

*Bauhinia variegata* in an amount of about 10.8-13.2% by weight of the total weight of the composition;

*Sphaeranthus indicus* in an amount of about 9.0-11.0% by weight of the total weight of the composition;

*Tecomella undulata* in an amount of about 9.0-11.0% by weight of the total weight of the composition;

*Chlorophytum borivilianum* in an amount of about 9.0-11.0% by weight of the total weight of the composition;

*Ficus racemosa* in an amount of about 9.0-11.0% by weight of the total weight of the composition; and

*Cyperus rotundus* in an amount of about 3.6-4.4% by weight of the total weight of the composition.

6. The pharmaceutical or medicinal herbal composition of claim 4, wherein the mixture of herbs comprises a mixture of active ingredients that have been extracted from the herbs.

7. A pharmaceutical or medicinal herbal preparation comprising:

a first composition comprising a mixture of herbs comprising: *Asparagus racemosa, Curcuma longa, Glycyrrhiza glabra, Momordica charantia, Tinospora cordifolia, Withania somnifera, Spirulina, Allium sativum, Emblica officinalis, Terminalia belerica,* and *Terminalia chebula*; and a second composition comprising a mixture of herbs comprising: *Moringa oleifera, Boerhavia diffusa, Onosma bracteatum, Bauhinia variegata, Sphaeranthus indicus, Tecomella undulata, Chlorophytum borivilianum, Ficus racemosa,* and *Cyperus rotundus.*

8. The pharmaceutical or medicinal herbal preparation of claim 7, wherein:

the first mixture of herbs comprises:

*Asparagus racemosa* in an amount of about 12.0-14.6% by weight of the total weight of the composition;

*Curcuma longa* in an amount of about 12.0-14.6% by weight of the total weight of the composition;

*Glycyrrhiza glabra* in an amount of about 12.0-14.6% by weight of the total weight of the composition;

*Momordica charantia* in an amount of about 12.0-14.6% by weight of the total weight of the composition;

*Tinospora cordifolia* in an amount of about 12.0-14.6% by weight of the total weight of the composition;

*Withania somnifera* in an amount of about 12.0-14.6% by weight of the total weight of the composition;

*Spirulina* in an amount of about 6.1-7.5% by weight of the total weight of the composition;

*Allium sativum* in an amount of about 6.0-7.4% by weight of the total weight of the composition;

*Emblica officinalis* in an amount of about 2.4-3.0% by weight of the total weight of the composition;

*Terminalia belerica* in an amount of about 1.8-2.2% by weight of the total weight of the composition; and

*Terminalia chebula* in an amount of about 1.8-2.2% by weight of the total weight of the composition;

the second mixture of herbs comprises:

*Moringa oleifera* in an amount of about 13.9-16.9% by weight of the total weight of the composition;

*Boerhavia diffusa* in an amount of about 14.1-16.1% by weight of the total weight of the composition;

*Onosma bracteatum* in an amount of about 12.6-15.8% by weight of the total weight of the composition;

*Bauhinia variegata* in an amount of about 10.8-13.2% by weight of the total weight of the composition;

*Sphaeranthus indicus* in an amount of about 9.0-11.0% by weight of the total weight of the composition;

*Tecomella undulata* in an amount of about 9.0-11.0% by weight of the total weight of the composition;

*Chlorophytum borivilianum* in an amount of about 9.0-11.0% by weight of the total weight of the composition;

*Ficus racemosa* in an amount of about 9.0-11.0% by weight of the total weight of the composition; and

*Cyperus rotundus* in an amount of about 3.6-4.4% by weight of the total weight of the composition.

9. The pharmaceutical or medicinal herbal preparation of claim 7, wherein the first and second mixtures of herbs comprise a mixture of active ingredients that have been extracted from the herbs.

10. The pharmaceutical or medicinal herbal preparation of claim 7, wherein the first and second mixtures of herbs are each administered in a form of at least one of the group comprising a gelatin capsule, a tablet, a liquid, and a syrup.

11. The pharmaceutical or medicinal herbal preparation of claim 7, for use in one of the following: improving the immune response, rejuvenating the immune system, and regulating the immune system.

12. The pharmaceutical or medicinal herbal preparation of claim 7, wherein the preparation is used as at least one of the group comprising an immunostimulant, an adaptogen, an antioxidant, an anxiolytic agent, an anti-stress agent, and an anti-tumor agent.

13. A method for preparing a pharmaceutical or medicinal herbal treatment preparation comprising:

harvesting the following herbal ingredients: *Asparagus racemosa, Curcuma longa, Glycyrrhiza glabra, Momordica charantia, Tinospora cordifolia, Withania somnifera, Spirulina, Allium sativum, Emblica officinalis, Terminalia belerica, Terminalia chebula, Moringa oleifera, Boerhavia diffusa, Onosma bracteatum, Bauhinia variegata, Sphaeranthus indicus, Tecomella*

*undulata*, *Chlorophytum borivilianum*, *Ficus racemosa*, and *Cyperus rotundus*;

grinding the herbal ingredients into a fine powder form;

purifying the herbal ingredients by at least one method selected from the group consisting of solvent extraction, FREON™ gas extraction, and carbon dioxide extraction;

preparing a first mixture of herbs by mixing the following herbal ingredients in the following amounts:

*Asparagus racemosa* in an amount of about 12.0-14.6% by weight of the total weight of the composition;

*Curcuma longa* in an amount of about 12.0-14.6% by weight of the total weight of the composition;

*Glycyrrhiza glabra* in an amount of about 12.0-14.6% by weight of the total weight of the composition;

*Momordica charantia* in an amount of about 12.0-14.6% by weight of the total weight of the composition;

*Tinospora cordifolia* in an amount of about 12.0-14.6% by weight of the total weight of the composition;

*Withania somnifera* in an amount of about 12.0-14.6% by weight of the total weight of the composition;

*Spirulina* in an amount of about 6.1-7.5% by weight of the total weight of the composition;

*Allium sativum* in an amount of about 6.0-7.4% by weight of the total weight of the composition;

*Emblica officinalis* in an amount of about 2.4-3.0% by weight of the total weight of the composition;

*Terminalia belerica* in an amount of about 1.8-2.2% by weight of the total weight of the composition; and

*Terminalia chebula* in an amount of about 1.8-2.2% by weight of the total weight of the composition;

preparing a second mixture of herbs by mixing the following herbal ingredients in the following amounts:

*Moringa oleifera* in an amount of about 13.9-16.9% by weight of the total weight of the composition;

*Boerhavia diffusa* in an amount of about 14.1-16.1% by weight of the total weight of the composition;

*Onosma bracteatum* in an amount of about 12.6-15.8% by weight of the total weight of the composition;

*Bauhinia variegata* in an amount of about 10.8-13.2% by weight of the total weight of the composition;

*Sphaeranthus indicus* in an amount of about 9.0-11.0% by weight of the total weight of the composition;

*Tecomella undulata* in an amount of about 9.0-11.0% by weight of the total weight of the composition;

*Chlorophytum borivilianum* in an amount of about 9.0-11.0% by weight of the total weight of the composition;

*Ficus racemosa* in an amount of about 9.0-11.0% by weight of the total weight of the composition; and

*Cyperus rotundus* in an amount of about 3.6-4.4% by weight of the total weight of the composition; and dispersing each of the first and second mixtures of herbs in an acceptable form of administration.

14. The method of claim 13, further comprising the step of blending the first and second mixtures of herbs to prepare homogenous mixtures of the herbal ingredients.

15. The method of claim 13, wherein the acceptable form of administration comprises at least one of a gelatin capsule, a tablet, a liquid, and a syrup.

16. The method of claim 13, wherein the first and second mixtures of herbs of the herbal treatment preparation are administered together.

17. The method of claim 13, wherein the preparation is used for at least one of the group comprising improving the immune response, rejuvenating the immune system, and regulating the immune system.

18. The method of claim 13, wherein the preparation is used as at least one of the group comprising an immunostimulant, an adaptogen, an antioxidant, an anxiolytic agent, an anti-stress agent, and an anti-tumor agent.

19. The method of claim 13, for use in the treatment of at least one of the group comprising cancer, human immunodeficiency virus (HIV), acquired immune deficiency syndrome (AIDS), and chronic fatigue syndrome.

* * * * *